(12) United States Patent
Bi et al.

(10) Patent No.: US 10,052,033 B2
(45) Date of Patent: Aug. 21, 2018

(54) SYSTEM AND METHOD FOR MOTION-ROBUST 3D MAGNETIC RESONANCE IMAGING OF VESSEL WALLS

(71) Applicants: Siemens Healthcare GmbH, Erlangen (DE); Cedars-Sinai Medical Center, Los Angeles, CA (US)

(72) Inventors: Xiaoming Bi, Oak Park, CA (US); Yutaka Natsuaki, Riverside, CA (US); Zhaoyang Fan, Hacienda Heights, CA (US); Debiao Li, South Pasadena, CA (US); Gerhard Laub, San Mateo, CA (US)

(73) Assignees: Siemens Healthcare GmbH, Erlangen (DE); Cedars-Sinai Medical Center, Los Angeles, CA (US)

( * ) Notice: Subject to any disclaimer, the term of this patent is extended or adjusted under 35 U.S.C. 154(b) by 416 days.

(21) Appl. No.: 15/017,788

(22) Filed: Feb. 8, 2016

(65) Prior Publication Data

US 2016/0266223 A1   Sep. 15, 2016

Related U.S. Application Data

(60) Provisional application No. 62/131,988, filed on Mar. 12, 2015.

(51) Int. Cl.
| | |
|---|---|
| *G01R 33/48* | (2006.01) |
| *G01R 33/56* | (2006.01) |
| *G01R 33/563* | (2006.01) |
| *A61B 5/02* | (2006.01) |
| *A61B 5/00* | (2006.01) |

(52) U.S. Cl.
CPC ........ *A61B 5/02007* (2013.01); *A61B 5/7207* (2013.01); *G01R 33/4826* (2013.01); *G01R 33/5607* (2013.01); *G01R 33/5635* (2013.01)

(58) Field of Classification Search
CPC ............ G01R 33/4826; G01R 33/5607; G01R 33/5635; A61B 5/02007; A61B 5/7207
See application file for complete search history.

(56) References Cited

U.S. PATENT DOCUMENTS

| | | | | |
|---|---|---|---|---|
| 7,941,204 | B1 * | 5/2011 | Wang ................. | G01R 33/4824 324/307 |
| 2011/0071382 | A1 * | 3/2011 | Miyazaki ........... | G01R 33/5635 600/413 |
| 2013/0314086 | A1 * | 11/2013 | Li .................... | G01R 33/56509 324/309 |

OTHER PUBLICATIONS

H.R. Underhill et al., MRI of carotid atherosclerosis: clinical implications and future directions, Nature Reviews Cardiology 2010;7:165-173.

(Continued)

*Primary Examiner* — Rodney Bonnette

(57) ABSTRACT

A magnetic resonance method and system are provided for providing improved 3D imaging of blood vessels and the like, which provides suppression of both blood and fat signals and is insensitive to subject motion, thereby facilitating improved visualization of vessel walls. The image data pulse sequence includes a plurality of pulse series, where each series includes a dark-blood sequence, a fat-suppression sequence, and a data readout sequence. Each data readout sequence samples a particular radial direction within each partition (Kz value) that passes through the Kz axis, and different radial orientations are sampled in subsequent series to provide a stack-of-stars sampling scheme.

20 Claims, 5 Drawing Sheets

(56) References Cited

OTHER PUBLICATIONS

T. Saam et al., Carotid plaque composition differs between ethno-racial groups: an MRI pilot study comparing mainland Chinese and American Caucasian patients, Arteriosclerosis, Thrombosis, and Vascular Biology 2005;5:611-616.
I. Koktzoglou et al., Diffusion-prepared segmented steady-state free precession: Application to 3D black-blood cardiovascar magnetic resonance of the thoracic aorta and carotid artery walls, Journal of Cardiovascular Magnetic Resonance 2007;9:33-42.
N. Balu et al., Carotid plaque assessment using fast 3D isotropic resolution black-blood MRI, Magnetic Resonance in Medicine 2011;65:627-637.
C. Stehning et al., Fast isotropic volumetric coronary MR angiography using free-breathing 30 radial balanced FFE acquisition, Magnetic Resonance in Medicine 2004;52:197-203.
Z. Fan prepared et al., 3D noncontrast MR angiography of the distal extremities using flow-sensitive dephasing (FSD)—balanced SSFP, Magnetic Resonance in Medicine 2009;62:1523-1532.
L. Li et al., Dante-prepared pulse trains: a novel approach to motion-sensitized and motion-suppressed quantitative magnetic resonance imaging, Magnetic Resonance in Medicine 2012;68:1423-1438.
H. Chandarana et al., Free-breathing radial 3D fat-suppressed T1-weighted gradient echo sequence: a viable alternative for contrast-enhanced liver imaging in patients unable to suspend respiration, Investigative Radiology 2011;46:648-653.

\* cited by examiner

SYSTEM AND METHOD FOR MOTION-ROBUST 3D MAGNETIC RESONANCE IMAGING OF VESSEL WALLS

CROSS REFERENCE TO RELATED APPLICATIONS

This application claims the benefit under 35 U.S.C. § 119(e) of U.S. Provisional Application No. 62/131,988 entitled MOTION-ROBUST, THREE-DIMENSIONAL BLACK-BLOOD CAROTID VESSEL WALL IMAGING USING MRI WITH BLACK-BLOOD PREPARATION AND STACK-OF-STARS SAMPLING TRAJECTORY, filed on Mar. 12, 2015 which is incorporated herein by reference in its entirety and to which this application claims the benefit of priority.

FIELD OF THE DISCLOSURE

The present disclosure relates to a magnetic resonance imaging (MRI) system and method for the visualization of vascular structures, such as the carotid artery wall. More specifically, certain magnetization preparations and k-space sampling schemes are combined to acquire volumetric carotid vessel wall images with optimal vessel wall-background imaging contrast, vessel wall sharpness, and robustness with respect to motion during the imaging procedure.

BACKGROUND INFORMATION

Assessment of plaque morphology and composition in carotid vessels is clinically important for early detection of vulnerable plaque, monitoring the progression of atherosclerotic plaque, and response to treatment for such plaque. Multi-contrast, 2D black-blood MRI (also referred to as "dark-blood" imaging) has been established as a non-invasive measure for characterizing the composition of carotid plaque. This vascular imaging technique includes suppression of the signal from flowing blood (rendering it "dark" or "black") rather than enhancing it as is done in bright-blood techniques. Rapidly-flowing or turbulent blood tends to exhibit a low signal because of phase-dispersion-induced signal losses. These effects may be further enhanced by application of flow-spoiling gradients, saturation bands, and/or inversion pulses. The lack of intraluminal signal allows the walls of vessels to be more clearly delineated during MR imaging. Thus, dark-blood techniques are often used in cardiac imaging and for evaluation of diseases of the vessel wall (e.g., to assess atherosclerotic plaque).

Dark-blood imaging techniques are described, e.g., in H. R. Underhill et al., MRI of carotid atherosclerosis: clinical implications and future directions, *Nature Reviews Cardiology* 2010; 7:165-173, and in T. Saam et al., Carotid plaque composition differs between ethno-racial groups: an MRI pilot study comparing mainland Chinese and American Caucasian patients, *Arteriosclerosis, Thrombosis, and Vascular Biology* 2005; 25:611-616. Both of these references are incorporated herein by reference in their entireties. The 2D carotid vessel imaging method described in these references is, however, limited by poor slice resolution and long imaging times.

A three-dimensional (3D) imaging technique for rapid assessment of plaque burden with a balanced steady-state free precession (SSFP) imaging readout is described, e.g., in I. Koktzoglou et al., Diffusion-prepared segmented steady-state free precession: Application to 3D black-blood cardiovascular magnetic resonance of the thoracic aorta and carotid artery walls, *Journal of Cardiovascular Magnetic Resonance* 2007; 9:33-42, which is incorporated herein by reference in its entirety. A 3D assessment of plaque burden using a spoiled gradient-echo sequence is described, e.g., in N. Balu et al., Carotid plaque assessment using fast 3D isotropic resolution black-blood MRI, *Magnetic Resonance in Medicine* 2011; 65:627-637, which is also incorporated herein by reference in its entirety. Compared to 2D methods, such 3D approaches can provide the benefits of volumetric spatial coverage and higher imaging efficiency. However, obtaining high-resolution volumetric images requires relatively long imaging times, e.g. on the order of 2-3 minutes. As a consequence, such 3D imaging procedures are frequently challenged by complex motion of carotid arteries originated from multiple sources, including arterial pulsation, swallowing, breathing, and involuntary motion of patient. For example, in a recent multi-center trial—described in L. Boussel et al., Atherosclerotic plaque progression in carotid arteries: monitoring with high-spatial-resolution MR imaging—multicenter trial, *Radiology* 2009; 252: 789-796—carotid MRI results from 52 out of 160 patients had to be excluded from analysis, with motion during the imaging procedure accounting for 46% of all rejections.

Radial k-space sampling schemes can oversample data in the central portion of k-space (e.g., close to the origin), and consequently may result in a reduction of undesirable motion-based image artifacts. For example, an isotropic 3D radial sampling approach with k-space data ordered in a "koosh-ball" type of trajectory can provide improved resistance to motion artifacts, as all data lines pass through the origin of k-space. This radial k-space sampling approach is described, e.g., in C. Stehning et al., Fast isotropic volumetric coronary MR angiography using free-breathing 30 radial balanced FFE acquisition, *Magnetic Resonance in Medicine* 2004; 52:197-203, which is incorporated herein by reference in its entirety.

In the isotropic 3D radial sampling technique described above, all k-space lines are equally weighted and contribute equally to the final image. However, it can be difficult or impossible to maintain the effect of magnetization preparation when using such an ordering scheme. Specifically, for MRI imaging of a carotid vessel, it is difficult to achieve consistent blood signal nulling and good fat saturation (to isolate these background signals from image data of the vessel walls themselves) using an isotropic 3D radial sampling of k-space.

Accordingly, it would be desirable to have a system and method for 3D magnetic resonance imaging of carotid vessels that addresses some of the shortcomings described above, for example, which can provide good nulling of fat and blood signals and also be insensitive to motion effects.

SUMMARY OF EXEMPLARY EMBODIMENTS

Exemplary embodiments of the present disclosure can provide systems and methods for 3D magnetic resonance (MR) imaging of vascular structures, e.g., a carotid wall or another vessel wall that is relatively insensitive to motion of the imaged volume. The imaging procedure described herein combines the advantages of both Cartesian and radial techniques, resulting in optimal background suppression (e.g., suppression of both blood and fat signals) while also reducing artifacts and image degradation arising from motion of the imaged volume.

In one embodiment, a magnetic resonance imaging system is provided that is configured to generate certain pulse sequences to obtain 3D image data for a volume to be imaged, where the pulse sequences include magnetization preparation sequences for suppression of both blood and fat signals, and a stack-of-stars (SoS) k-space sampling technique to obtain image data that oversamples image data near the Kz axis in k-space to provide insensitivity to motion effects. In a further embodiment, a method for imaging vessel walls and the like is provided that includes providing such pulse sequences using an MR imaging system to obtain image data and reconstruct images from such data.

An imaging pulse sequence in accordance with embodiments of the present disclosure include a plurality of repeated series, where each series includes a dark-blood (DB) 3D prototype sequence and a fat-saturation (FS) pulse sequence, followed immediately or shortly thereafter by a data readout (acquisition) sequence. The interval between the DB and FS sequences and the subsequent readout sequence is preferably short enough that the conditioning or selective signal suppression provided by the DB and FS sequences will be effective during the readout sequence. Only a portion of the k-space lines are acquired after the DB and FS magnetization preparation modules for each series in the overall sequence.

The DB preparation sequence or module that is used to null the blood signals within a large volume generally includes a plurality of non-selective RF pulses with spoiling gradients provided between these RF pulses. In certain embodiments, the DB sequence can be a flow-sensitive dephasing (FSD) sequence. In further embodiments of the disclosure, the DB sequence can be a delay alternating with nutation for tailored excitation (DANTE) preparation sequence. In still further embodiments, other configurations of non-selective dark-blood preparation sequences can be used. Various known non-selective fat saturation sequences can be used in embodiments of the disclosure.

The imaging pulse sequence includes a stack-of-stars (SoS) sampling of k-space to obtain the image data. This sampling geometry includes sampling a plurality of lines in a distribution of radial directions in the Kx-Ky planes, where such radial lines (or "stars") are further sampled in a Cartesian order in the partition direction Kz.

In each readout sequence (or train) within one of the plurality of series, data for the same radial view (or projection angle) is acquired for all partitions (e.g., for all values of Kz). Each subsequent readout sequence (for a different series within the imaging sequence) samples k-space data for a different particular projection angle in the Kx-Ky planes for all Kz values in the range being sampled. This data readout procedure is repeated for additional series within the imaging pulse sequence until the entire set of k-space data is collected.

In some exemplary embodiments, two or more projection angles can be sampled during a single data readout sequence, where each projection angle is sampled in the plurality of Kx-Ky planes spanning the range of Kz values being sampled.

In certain embodiments, the acquisition order for radial lines within each Kx-Ky plane can be sequential, such that each k-space trajectory within a Kx-Ky plane is adjacent to the trajectory of the previous readout sequence in the overall "star" pattern of radial lines. In further embodiments, the projection angles for the sampled lines can be interleaved, such that k-space trajectories in successive readout sequences lie between previously-obtained trajectories (in an angular sense) associated with prior readout sequences within each Kx-Ky plane.

Within each data readout sequence (at a fixed projection angle), the individual radial lines sampled in k-space can begin at the center partition (Kz=0), with subsequent radial lines sampled at increasing distances from Kz=0 (e.g., with increasing absolute values of Kz). In further embodiments, variations on this sequence in the Kz direction for collecting data during a single readout sequence can be used, although it may be preferable to sample radial lines having small Kz values near the beginning of each readout sequence.

In further embodiments of the disclosure, volumetric image data obtained using the image data sequences described herein can be processed to generate two-dimensional image planes within the imaged volume. Such images can be generated, e.g., as coronal, axial, and/or sagittal views, or as views contained in other planar orientations.

BRIEF DESCRIPTION OF THE DRAWINGS

Further objects, features and advantages of the present disclosure will become apparent from the following detailed description taken in conjunction with the accompanying figures showing illustrative embodiments, results and/or features of the exemplary embodiments of the present disclosure, in which.

While the present disclosure will now be described in detail with reference to the figures, it is done so in connection with the illustrative embodiments and is not limited by the particular embodiments illustrated in the figures. It is intended that changes and modifications can be made to the described embodiments without departing from the true scope and spirit of the present invention as defined by the appended claims.

DETAILED DESCRIPTION OF EXEMPLARY EMBODIMENTS

The present disclosure relates to methods and systems for providing improved imaging of carotid vessel walls, other vessel walls and/or cardiac chamber walls, as well as plaque that may be present, while being insensitive to motion effects/artifacts during the imaging procedure.

Figure 1:
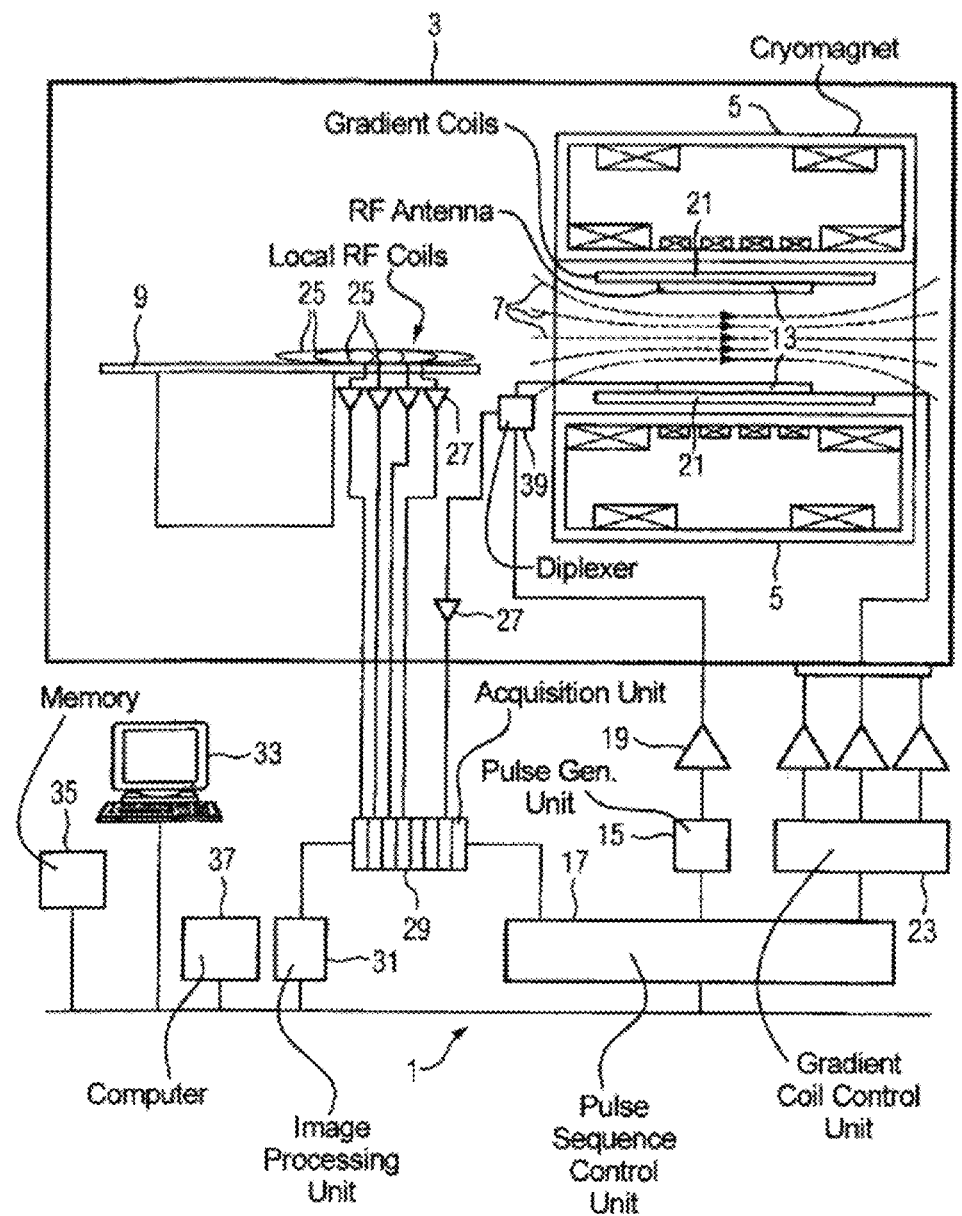
FIG. 1 schematically illustrates the basic components of a magnetic resonance imaging system constructed and operating in accordance with embodiments of the present disclosure.

FIG. 1 schematically shows the design of a magnetic resonance system 1 with certain components in accordance with embodiments of the present disclosure. The MR system 1 is configured, inter alia, to provide various magnetic fields tuned to one another as precisely as possible in terms of their temporal and spatial characteristics to facilitate examination of portions of a subject's body using magnetic resonance imaging techniques.

A strong magnet 5 (typically a cryomagnet), which may have a tunnel-shaped opening, is provided in a radio-frequency (RF) shielded measurement chamber 3 to generate a static, strong base (or polarizing) magnetic field 7. The strength of the base magnetic field 7 is typically between 1 Tesla and 7 Tesla, although lower or higher field strengths can be provided in certain embodiments. A body or a body part to be examined (not shown) can be positioned within the substantially homogeneous region of the base magnetic field 7, e.g., provided on a patient bed 9.

Excitation of nuclear spins of certain atoms within the body can be provided via magnetic RF excitation pulses that are radiated using an RF antenna 13, such as a body coil. Other configurations of RF coils or antennas can also be provided in further embodiments, and such configurations may be adapted for particular portions of the subject anatomy to be imaged. The RF excitation pulses are generated by a pulse generation unit 15 that is controlled by a pulse sequence control unit 17. After an amplification by a radio-frequency amplifier 19, the RF pulses are relayed to the RF antenna 13. The exemplary RF system shown in FIG. 1 is a schematic illustration, and particular configurations of the various components may vary from that illustrated in exemplary embodiments of the disclosure. For example, the MR system 1 can include a plurality of pulse generation units 15, a plurality of RF amplifiers 19, and/or a plurality of RF antennas 13, and each of which may have various configurations depending on the body parts being imaged.

The magnetic resonance system 1 further includes gradient coils 21 that can provide directionally and temporally varied magnetic gradient fields for selective excitation and spatial encoding of the RF signals that are emitted and/or received by the RF antenna(s) 13. The gradient coils 21 are typically oriented along the three primary axes (x- y- and z-directions), although other or additional orientations may be used in certain embodiments. Pulsed current supplied to the gradient coils 21 can be controlled by a gradient coil control unit 23 that, like the pulse generation unit 15, is connected with the pulse sequence control unit 27. By controlling the pulsed current supplied to the gradient coils 21, transient gradient magnetic fields in the x-, y-, and z-directions can be superimposed on the static base magnetic field B0. This makes it possible to set and vary, for example, the directions and magnitudes of a slice gradient magnetic field Gs, a phase encode gradient magnetic field Ge, and a read (frequency encode) gradient magnetic field Gr, which can be synchronized with emission and detection of RF pulses. Such interactions between RF pulses and transient magnetic fields can provide spatially selective excitation and spatial encoding of RF signals.

RF signals emitted by the excited nuclear spins can be detected by the RF antenna 13 and/or by local coils 25, amplified by associated radio-frequency preamplifiers 27, and processed further and digitized by an acquisition unit 29. In certain embodiments where a coil 13 (such as, for example, a body coil) can be operated both in transmission mode and in acquisition mode (e.g., it can be used to both emit RF excitation pulses and receive RF signals emitted by nuclear spins), the correct relaying of RF energy is regulated by an upstream transmission-reception diplexer 39.

An image processing unit 31 can generate one or more images based on the RF signals that represent image data. Such images can be presented to a user via an operator console 33 and/or be stored in a memory unit 35. A processor arrangement 37 can be provided in communication with the memory unit 35, and configured to execute computer-executable instructions stored in the memory unit 35 to control various individual system components. For example, the processor arrangement 37 can be configured by programmed instructions to control components such as, e.g., the gradient coil control unit 23, the pulse generation unit 15, and/or the pulse sequence control unit 27 to generate particular sequences of RF pulses and magnetic field variations, process and/or manipulate image data, etc., according to exemplary embodiments of the disclosure described herein.

Embodiments of the present disclosure can provide an MR imaging system 1, such as that shown in FIG. 1, which is configured to provide 3D MR imaging sequences for improved imaging of vascular structures such as vessel walls (e.g. carotid walls) and plaque that may be present thereon, as described in the embodiments herein. The image data obtained in accordance with embodiments of the present disclosure is also insensitive to motion during the imaging procedure. The MR system 1 can be further configured to process the resulting image data to generate images of the vessel walls of interest.

Figure 2:
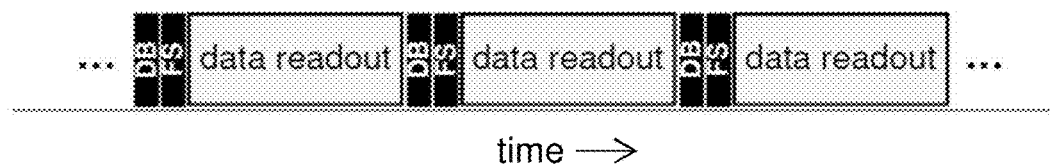
FIG. 2 is a schematic illustration of an exemplary image data sequence that includes a plurality of series, where each series includes a dark-blood sequence and a fat-suppression sequence followed by a data readout sequence, and where each data readout sequence samples a portion of the k-space data used to generate an image.

A schematic illustration of an exemplary imaging sequence of RF pulse signals and applied magnetic field gradients, in accordance with embodiments of the present disclosure, is shown in FIG. 2. The exemplary imaging sequence includes a plurality of repeated series, where each series includes a dark-blood (DB) 3D prototype sequence or module followed by a fat-saturation (FS) pulse sequence/module and a data readout (acquisition) sequence. In certain embodiments, the FS sequence can precede the DB sequence prior to a data readout sequence. However, because the FS sequence is shorter than the DB sequence, it may be preferable to provide the FS sequence after the DB sequence, which can also increase the effects of the FS sequence during the data readouts. This segmented imaging sequence is particularly effective for carotid vessel wall imaging. For example, the overall image data acquisition is segmented so that only a portion of the k-space lines are acquired after each instance of the DB and FS magnetization preparation modules. Details of the k-space lines sampled within each DB/FS/readout series of the overall imaging sequence are described herein below. This configuration of the overall imaging sequence facilitates maintenance of the blood nulling and fat saturation effects during each of the 3D data readout sequences.

A conventional 2D double-inversion sequence for dark-blood imaging includes a non-selective inversion pulse immediately followed by a selective inversion pulse. Such dark-blood magnetization sequences rely on non-inverted blood flowing from outside to within the imaging slice during the inversion recovery time (TI). This approach works reasonably well for single-slice 2D imaging procedures. However, during 3D imaging procedures, the blood exchange during the TI time interval is not sufficient for the larger volumes being imaged. Accordingly, to facilitate effective blood nulling for a 3D image data readout, a non-selective preparation module can be used to null the blood signals within a large volume in embodiments of the present disclosure.

Figure 3:
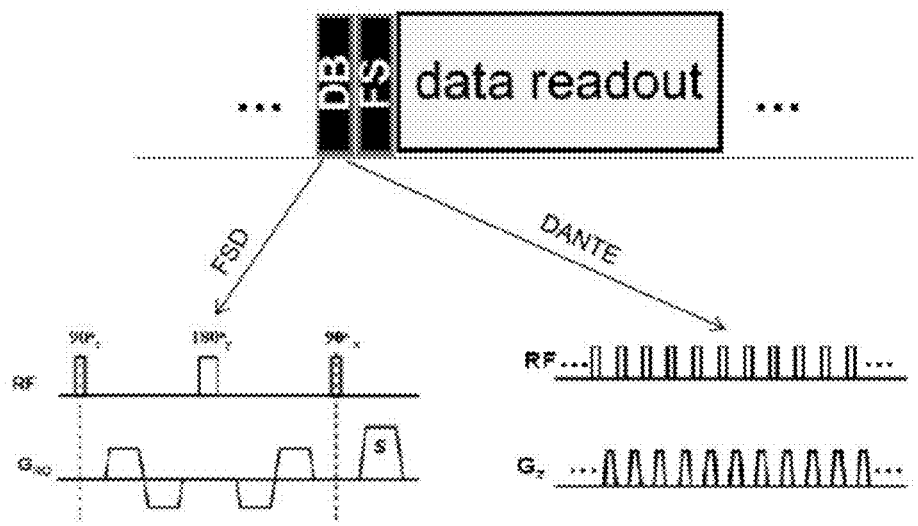
FIG. 3 is an illustration of a single series from the image data pulse sequence shown in FIG. 2, with two alternate options for the type of dark-blood sequence that may be used with embodiments of the disclosure.

FIG. 3 illustrates two types of dark-blood preparation modules that may be used in embodiments of the present disclosure. The upper portion of FIG. 3 shows a single series that is a repeated portion of the overall imaging sequence shown in FIG. 2, where the series includes a 3D DB sequence, an FS pulse sequence, and a data readout sequence. The dark-blood (DB) sequence generally includes a plurality of non-selective RF pulses with spoiling gradients provided between these RF pulses.

In certain embodiments, the DB sequence can be a flow-sensitive dephasing (FSD) sequence. This type of magnetization preparation sequence is described, e.g., in N. Balu et al. (2011), or in Z. Fan et al., 3D noncontrast MR angiography of the distal lower extremities using flow-sensitive dephasing (FSD)-prepared balanced SSFP, *Magnetic Resonance in Medicine* 2009; 62:1523-1532, which is incorporated herein by reference in its entirety. An exemplary FSD sequence is schematically illustrated in the lower-left portion of FIG. 3. Other variation of FSD sequences can also be used in embodiments of the present disclosure.

In further embodiments of the disclosure, the DB sequence can be a delay alternating with nutation for tailored excitation (DANTE) preparation sequence, as illustrated schematically in the lower-right portion of FIG. 3. This type of magnetization preparation sequence for dark-blood imaging, which can include a nonselective RF pulse train alternating with gradient pulses (both having short repetition times), is described, e.g., in L. Li et al., DANTE-prepared pulse trains: a novel approach to motion-sensitized and motion-suppressed quantitative magnetic resonance imaging, *Magnetic Resonance in Medicine* 2012; 68:1423-1438, which is incorporated herein by reference in its entirety.

To improve the motion robustness during the imaging procedure, a stack-of-stars (SoS) trajectory can be used to sample image data along radial k-space lines in the Kx-Ky planes, and in a Cartesian order in the partition direction Kz (e.g., in a plurality of Kx-Ky planes having different Kz values). This general radial k-space sampling approach has been described previously for body imaging, e.g., in H. Chandarana et al., Free-breathing radial 3D fat-suppressed T1-weighted gradient echo sequence: a viable alternative for contrast-enhanced liver imaging in patients unable to suspend respiration, *Investigative Radiology* 2011; 46:648-653, which is incorporated herein by reference in its entirety.

In each readout train, data for the same radial view (or projection angle) is acquired for all partitions (e.g., for all values of Kz). Each subsequent readout train (which follows a new dark-blood magnetization sequence DB and a fat-suppression sequence FS, as shown in FIG. 2) acquires or samples k-space data for a different particular projection angle in the Kx-Ky planes for all Kz values. This data readout procedure is repeated until the entire set of k-space data is collected.

Figure 4:
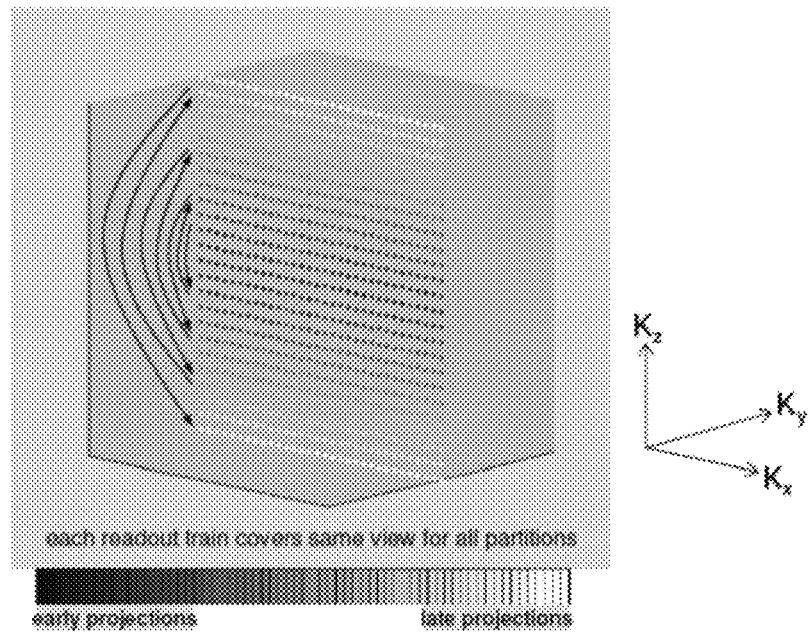
FIG. 4 is an illustration of an exemplary sequence for sampling k-space lines within a single readout sequence at a particular radial direction for a plurality of partition (Kz) values.

FIG. 4 illustrates a set of k-space trajectory lines that are sampled during a single data readout sequence. Each of these lines lies in a different Kx-Ky plane (e.g., each line has a different Kz value), and passes through the origin of that plane (e.g., Kx=0, Ky=0, which represents the intersection of each Kx-Ky plane with the Kz axis). The projection angle of each line is the same, that is, the direction of each line is the same relative to the Kx and Ky axes for different Kz values within a single data readout sequence. The shade of the dotted sampling lines in this figure indicate the sampling order of these lines, which begin near the origin in k-space (Kz=0) and progress in increasing absolute values of Kz. The arrows in FIG. 4 also indicate this sampling sequence with respect to Kz values for k-space lines having a single projection angle.

In further embodiments, a plurality of projection angles can be sampled over the various Kx-Ky planes for some or all of the individual data readout sequences. For example, 2 or 3 different projection angles can be sampled in k-space for a range of Kz values during a single data readout sequence that follows a particular DB and FS sequence. Such multi-line sampling can reduce the overall imaging or scan time needed to acquire image data for the volume of interest. The selection of how many projection angles are sampled for each data readout sequence can be selected, e.g., based on the desired image resolution, particular imaging protocol being used, capabilities of the MRI system, etc. Sampling a plurality of sets of projection angles in a single readout sequence will increase the duration of the readout sequence. Accordingly, the effects of the DB and FS sequences may be reduced or diminished in the later portion of such longer readout sequences.

Figure 5:
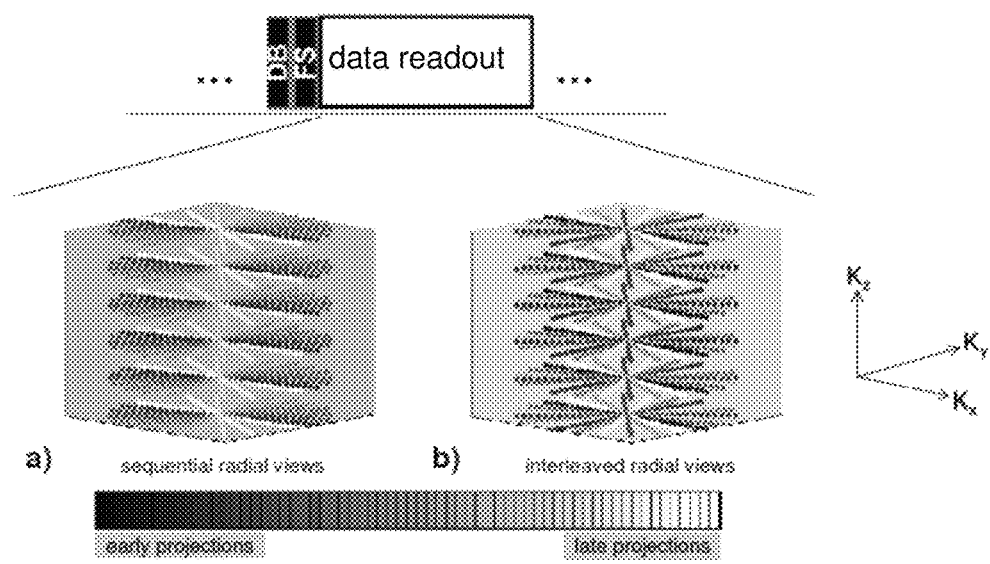
FIG. 5 is a schematic illustration of both sequential and interleaved sampling orders for radial lines within each Kz plane, where the radial lines within each Kz plane are obtained in successive readout sequences within the image data pulse sequence.

In certain embodiments, the projection angle for the sampled lines can be sequential, such that the projection angle increases by a certain value in each successive readout sequence, and each k-space trajectory is adjacent to the trajectory of the previous readout sequence within each Kx-Ky plane. This sequential radial scheme is illustrated, e.g., in FIG. 5(a). The angles within each Kx-Ky plane increase uniformly from an initial projection angle, as indicated by the dotted sampling lines progressing from black to white in this figure.

In further embodiments, the projection angles for the sampled lines can be interleaved, such that the projection angle increases by larger values in successive readout sequences, where later-obtained k-space trajectories lie between previously-obtained trajectories (in an angular sense) of previous readout sequences within each Kx-Ky plane. This interleaved radial scheme is illustrated, e.g., in FIG. 5(b). The angles of lines sampled within each Kx-Ky plane are interspersed with respect to time, as indicated by the dotted sampling lines from black to white being 'mixed' in each Kz plane in this figure.

In general, a sequential sampling of the projection lines (with respect to increasing angle in the Kx-Ky plane) can facilitate a smooth alternation of k-space trajectories from one projection angle to the next, thereby reducing undesirable eddy currents that may be induced by variation of encoding gradients. For example, radial sampling of k-space using an interleaved order of projection angles leads to larger shifts in radial view for successive sampling trajectories, which is typically associated with higher eddy currents. However, an interleaved sample ordering of projection angles can facilitate greater flexibility during image reconstruction. For example, k-space data that may be corrupted by motion of the subject at a certain time period during the image scan will spread out evenly into different k-space region if interleaved sampling is used. Such data can be effectively eliminated from reconstruction without causing significant loss of data in certain spatial domains, if needed.

For either sequential or interleaved sample acquisition, the central k-space data are over-sampled for each individual partition (e.g. for the set of radial lines sampled in each Kx-Ky plane having a particular Kz value). As noted above, this results from each radial line passing through the origin of the corresponding Kx-Ky plane, such that the areal density of sampled lines is greatest near the origin and diminishes with distance from the Kz axis. This oversampling near the Kz axis generates image data that is less sensitive to motion during the image acquisition procedure.

To optimize the effect of magnetization preparation, central k-space data is preferably acquired immediately after the DB and FS preparation modules. For example, as illustrated in FIG. 3, this can be realized by utilizing a centric order in the partition (Kz) direction. With such an ordering scheme, each data readout sequence (at a fixed projection angle) begins from the center partition (Kz=0) and moves uniformly toward outer partitions (increasing absolute values of Kz). This sampling order can be described as 0, $\Delta$Kz, $-\Delta$Kz, 2$\Delta$Kz, $-2\Delta$Kz, 3$\Delta$Kz, $-3\Delta$Kz, etc., where $\Delta$Kz represents the distance between adjacent partition planes (Kx-Ky planes) in the sampled k-space, and each term in the sequence represents the distance of each sampled plane from the origin (Kz=0) along the Kz axis. In further embodiments, variations of this sequence in the Kz direction for collecting data during a single readout sequence can be used. In general, it is preferable to begin such data collection in Kx-Ky planes that are closer to Kz=0 (e.g. for smaller Kz values), such that data closest to the origin of k-space is collected sooner following the various DB and FS magnetization preparation modules.

Figure 6:
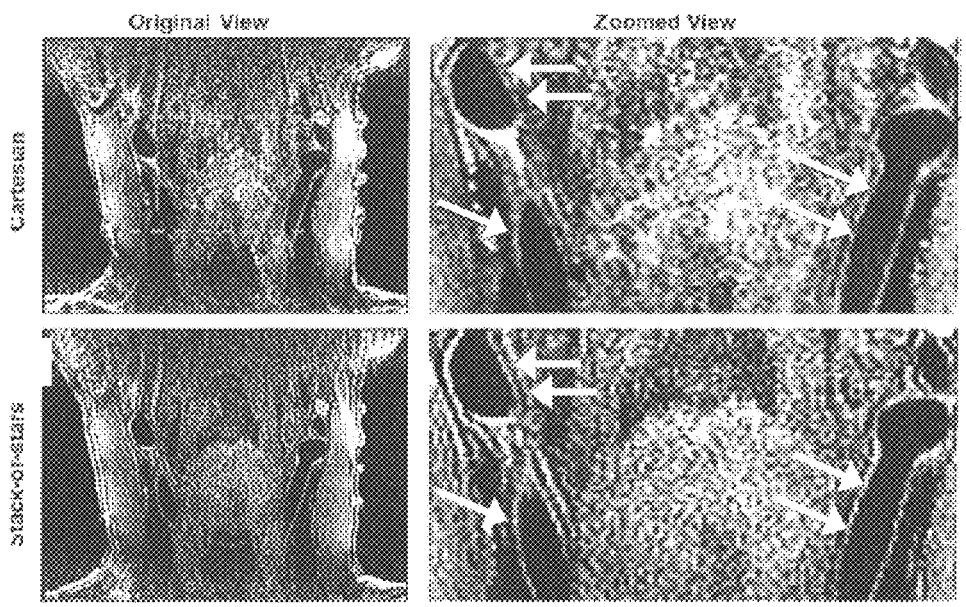
FIG. 6 shows 3D images of a volume containing blood vessels that were obtained using a conventional Cartesian sampling scheme and a stack-of-stars sampling scheme in accordance with embodiments of the present disclosure.

The top row of FIG. 6 shows an exemplary 3D image of a tissue volume containing blood vessels that was acquired using a conventional method with a Cartesian k-space sampling scheme. A magnified view of the central portion of the left-hand image is provided to the right of this image. The bottom half of FIG. 6 shows corresponding images of the same volume using an imaging method and apparatus according to certain embodiments of the present disclosure, which include a stack-of-stars k-space sampling scheme. Imaging parameters were matched for the two imaging techniques shown in FIG. 6 as follows:

field-of-view=14×14 cm$^2$;
64 partitions;
192 radial views (for stack-of-stars sampling) or 192 phase-encoding lines (for Cartesian sampling) with 192 readout resolution;
isotropic acquisition voxel size=0.73×0.73×0.73 mm$^3$;
flip angle=8°;
TR/TE=8.0/2.5 msec;
12.5% slice oversampling; and
spoiled gradient-echo readout.

A conventional FSD module was utilized for blood nulling in this exemplary comparison of imaging methods.

The images obtained using a conventional Cartesian sampling method (upper part of FIG. 6) reveals some corruption of the wall image data, as indicated by the white arrows in the right-hand zoomed view. In contrast, 3D images of the same volume obtained in accordance with embodiments of the disclosure show improved imaging of the vessel walls, as indicated by the white arrows in the lower-right portion of FIG. 6.

Figure 7:
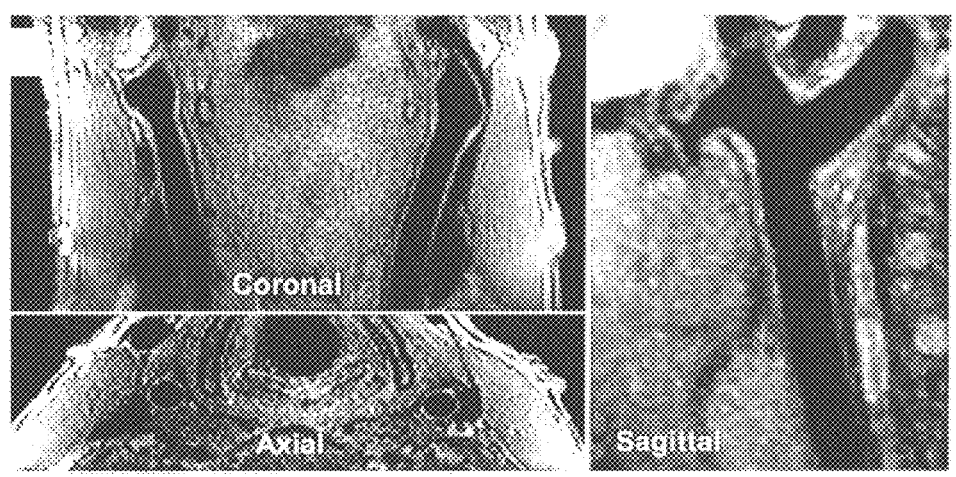
FIG. 7 shows three orthogonal planar images obtained from a 3D image data set that was obtained in accordance with embodiments of the present disclosure.

In further embodiments of the disclosure, volumetric image data obtained using the systems and methods described herein can be reformatted or processed to visualize a vessel wall from particular angles. For example, FIG. 7 shows an example of maximum-intensity-projection (MIP) operations applied to a stack-of-stars image data set. In these exemplary images, it is shown that the carotid vessel wall can be assessed from coronal, axial and/or sagittal views. This exemplary analysis indicates the advantages of using 3D (volumetric) imaging techniques for improved and more robust visualization of vessels.

To demonstrate the motion robustness of the systems and methods described herein, experiments were performed to collect carotid wall images without and with motion of the imaged volume, using both conventional Cartesian k-space data acquisition and a stack-of-stars method in accordance with embodiments of the present disclosure. The images obtained without motion using Cartesian and radial stack-of-stars methods (FIGS. 8(a) and 8(b), respectively) exhibit comparable quality. Further 3D images of the same volume were then obtained, with subject instructed to move (swallow and move the head slightly) during the motion-inclusive imaging procedures. The arrows in FIG. 8(c) identify image degradation/corruption around the vessel walls in the Cartesian image that was caused by the motion of the subject. In contrast, the image quality around the vessel walls was preserved in the image shown in FIG. 8(d), even though the subject underwent motion similar to that in FIG. 8(c) during the imaging procedure.

Figure 9:
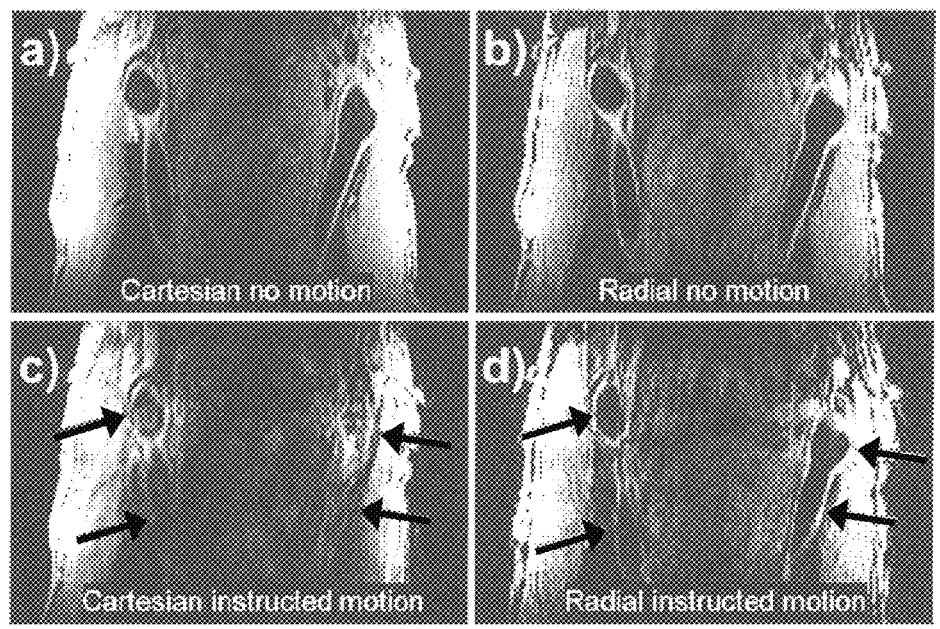
FIG. 9 shows a further set of 3D images of a volume containing blood vessels that were obtained without and with subject motion that were obtained using both a conventional Cartesian sampling scheme and a stack-of-stars sampling scheme in accordance with embodiments of the present disclosure.

FIG. 9 shows another exemplary set of images that were generated to demonstrate the efficacy of the systems and methods described herein to obtain improved-quality images of vessel walls, even when the subject moves during the imaging procedure. All of the images in FIG. 9 were obtained with matched protocol settings, including a 3D spatial resolution (voxel size) of 0.83×0.83×0.83 mm$^3$. The total imaging time for each 3D image shown in FIG. 9 was 3'12".

Figure 8:
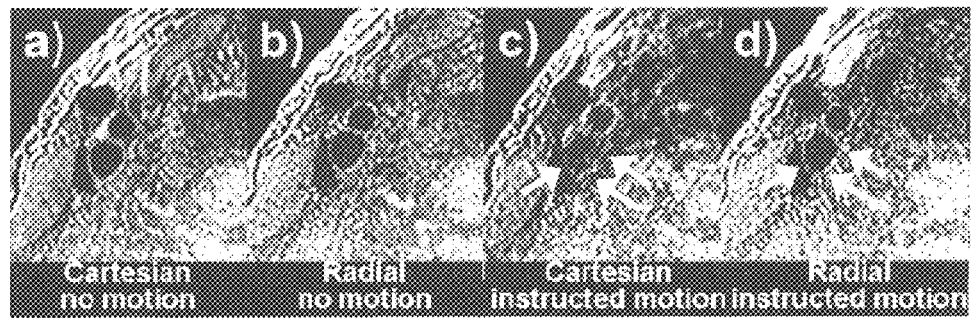
FIG. 8 shows a set of 3D images of a volume containing blood vessels that were obtained without and with subject motion that were obtained using both a conventional Cartesian sampling scheme and a stack-of-stars sampling scheme in accordance with embodiments of the present disclosure.

Similar to FIG. 8, two 3D images were obtained without motion using Cartesian and radial stack-of-stars methods (FIGS. 9(a) and 9(b), respectively). These different imaging procedures exhibit substantially similar quality in the absence of subject motion. The 3D images shown in FIGS. 9(c) and 9(d) of the same volume were obtained with the subject instructed to swallow once every 30 seconds while these images were being obtained. The arrows in FIG. 9(c) show some motion effects around the vessel walls in the Cartesian-sampled image. Again, the imaging of the vessel walls in the image shown in FIG. 9(d) (obtained using the exemplary system and methods described herein) is of higher quality as indicated by the arrows, thereby demonstrating the robustness of the systems and methods described herein with respect to subject motion during the imaging procedure.

The foregoing merely illustrates the principles of the present disclosure. Various modifications and alterations to the described embodiments will be apparent to those skilled in the art in view of the teachings herein. It will thus be appreciated that those skilled in the art will be able to devise numerous techniques which, although not explicitly described herein, embody the principles of the present disclosure and are thus within the spirit and scope of the present disclosure.

What is claimed is:
1. A method for 3D imaging of blood vessels in a magnetic resonance (MR) system, comprising the steps of:
 (a) generating a 3D image data set from a volume of a subject to be imaged using an imaging pulse sequence, wherein:

(i) the imaging pulse sequence comprises a plurality of imaging series;

(ii) each imaging series comprises a dark-blood sequence, a fat-suppression sequence, and a data readout sequence that follows both the dark-blood sequence and the fat-suppression sequence;

(iii) each data readout sequence samples data along a plurality of lines in k-space, wherein each line of the plurality of lines has a common radial direction in the Kx-Ky plane and a different Kz value, and passes through the Kz axis; and (iv) data readout sequences corresponding to different series of the imaging pulse sequence sample lines in k-space having different radial directions in the Kx-Ky plane, and (b) generating an image of at least a portion of the volume based at least in part on the 3D image data set.

2. The method of claim 1, wherein the dark-blood sequence precedes the fat-suppression sequence in each imaging series.

3. The method of claim 1, wherein the fat-suppression sequence precedes the dark-blood sequence in each imaging series.

4. The method of claim 1, wherein the dark-blood sequence is a flow-sensitive dephasing sequence.

5. The method of claim 1, wherein the dark-blood sequence is a delay alternating with nutation for tailored excitation (DANTE) sequence.

6. The method of claim 1, wherein each data readout sequence samples data along a further plurality of lines in k-space, wherein each line of the further plurality of lines has a second common radial direction in the Kx-Ky plane and a different Kz value, and passes through the Kz axis.

7. The method of claim 1, wherein the data readout sequences of the imaging pulse sequence sample lines in k-space having different radial directions in a sequential radial order.

8. The method of claim 1, wherein the data readout sequences of the imaging pulse sequence sample lines in k-space having different radial directions in an interleaved radial order.

9. The method of claim 1, wherein the plurality of radial lines sampled within each data readout sequence are sampled in an order of increasing distance from Kz=0 in k-space.

10. The method of claim 1, wherein the data readout sequences are spoiled gradient-echo readout sequences.

11. A magnetic resonance (MR) system for 3D imaging of blood vessels in a magnetic resonance (MR) system, comprising:

a radio frequency (RF) signal generator and a magnetic field gradient generator which are together configured to provide a an imaging pulse sequence comprising a plurality of RF pulse sequences and magnetic field gradient sequences for acquisition of 3D image data; and an image processing unit configured to generate MR images of a volume of interest based on the 3D image data, wherein:

the imaging pulse sequence comprises a plurality of imaging series;

each imaging series comprises a dark-blood sequence, a fat-suppression sequence, and a data readout sequence that follows both the dark-blood sequence and the fat-suppression sequence;

each data readout sequence samples data along a plurality of lines in k-space, wherein each line of the plurality of lines has a common radial direction in the Kx-Ky plane and a different Kz value, and passes through the Kz axis; and data readout sequences corresponding to different series of the imaging pulse sequence sample lines in k-space having different radial directions in the Kx-Ky plane.

12. The system of claim 11, wherein the dark-blood sequence precedes the fat-suppression sequence in each imaging series.

13. The system of claim 11, wherein the fat-suppression sequence precedes the dark-blood sequence in each imaging series.

14. The system of claim 11, wherein the dark-blood sequence is a flow-sensitive dephasing sequence.

15. The system of claim 11, wherein the dark-blood sequence is a delay alternating with nutation for tailored excitation (DANTE) sequence.

16. The system of claim 11, wherein each data readout sequence samples data along a further plurality of lines in k-space, wherein each line of the further plurality of lines has a second common radial direction in the Kx-Ky plane and a different Kz value, and passes through the Kz axis.

17. The system of claim 11, wherein the data readout sequences of the imaging pulse sequence sample lines in k-space having different radial directions in a sequential radial order.

18. The system of claim 11, wherein the data readout sequences of the imaging pulse sequence sample lines in k-space having different radial directions in an interleaved radial order.

19. The system of claim 11, wherein the plurality of radial lines sampled within each data readout sequence are sampled in an order of increasing distance from Kz=0 in k-space.

20. The system of claim 11, wherein the data readout sequences are spoiled gradient-echo readout sequences.

* * * * *